United States Patent [19]

Boeck et al.

[11] Patent Number: 4,663,282
[45] Date of Patent: * May 5, 1987

[54] GLYCOPEPTIDE ANTIBIOTIC CUC/CSV AND PROCESS FOR ITS PRODUCTION

[75] Inventors: LaVerne D. Boeck; Gladys M. Clem, both of Indianapolis; Charles L. Hershberger, New Palestine; Marie T. Anderson; Karl H. Michel, both of Indianapolis, all of Ind.

[73] Assignee: Eli Lilly and Company, Indianapolis, Ind.

[*] Notice: The portion of the term of this patent subsequent to May 6, 2003 has been disclaimed.

[21] Appl. No.: 729,785

[22] Filed: May 2, 1985

Related U.S. Application Data

[62] Division of Ser. No. 544,338, Oct. 21, 1983, Pat. No. 4,537,715.

[51] Int. Cl.$^4$ .............. C12P 21/00; C12P 21/02; C12N 1/20; C12R 1/045
[52] U.S. Cl. ........................ 435/68; 435/70; 435/253; 435/827
[58] Field of Search ............ 435/253, 827, 68, 70

[56] References Cited

U.S. PATENT DOCUMENTS

| | | | |
|---|---|---|---|
| 3,928,571 | 12/1975 | Raun | 424/118 |
| 3,952,095 | 4/1976 | Hamill et al. | 424/118 |
| 4,064,233 | 12/1977 | Hamill et al. | 424/118 |
| 4,115,552 | 9/1978 | Hamill et al. | 424/118 |
| 4,322,343 | 3/1982 | Debono | 260/112.5 R |
| 4,322,406 | 3/1982 | Debono et al. | 424/118 |

*Primary Examiner*—Thomas G. Wiseman
*Assistant Examiner*—Jayme A. Huleatt

*Attorney, Agent, or Firm*—Nancy J. Harrison; Leroy Whitaker

[57] ABSTRACT

New glycopeptide antibiotic CUC/CSV which has the formula:

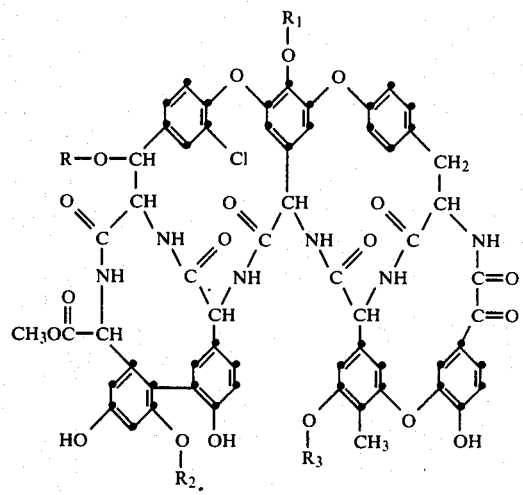

wherein
R is L-ristosaminyl;
$R_1$ is the disaccharide mannosyl-glucosyl; and
$R_2$ and $R_3$ are mannosyl, and its salts, particularly the pharmaceutically acceptable salts, are useful new antibiotics are active against gram-positive bacteria and increase feed-efficiency utilization and enhance milk production in ruminants.

3 Claims, No Drawings

GLYCOPEPTIDE ANTIBIOTIC CUC/CSV AND PROCESS FOR ITS PRODUCTION

This application is a division of application Ser. No. 544,338, filed 10/21/83, now U.S. Pat. No. 4,537,715, issued Aug. 27, 1985.

SUMMARY OF THE INVENTION

This invention provides a new glycopeptide antibiotic called CUC/CSV and processes for its preparation (1) by cosynthesis of two new strains of *Actinoplanes missouriensis* or (2) by bioconversion of actaplanin factor A using either of the new *A. missouriensis* strains. Compound CUC/CSV has formula 1:

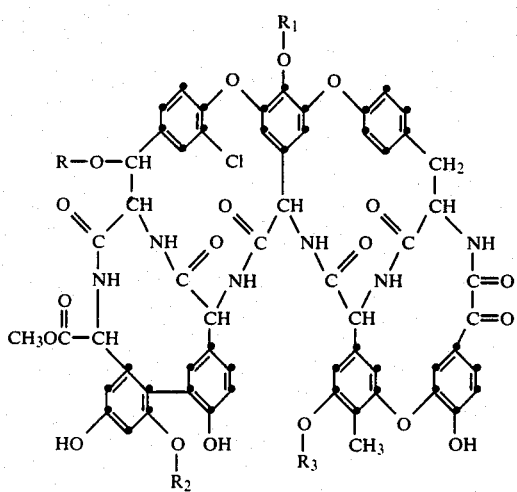

wherein
R is L-ristosaminyl;
$R_1$ is the disaccharide mannosyl-glucosyl; and
$R_2$ and $R_3$ are mannosyl. CUC/CSV and its salts, particularly the pharmaceutically acceptable salts, are useful new antibiotics. They are active against gram-positive bacteria and increase feed-efficiency utilization in animals and enhance milk production in ruminants.

DETAILED DESCRIPTION OF THE INVENTION

This invention relates to the new glycopeptide antibiotic of formula 1. This antibiotic, which has been designated CUC/CSV, was first obtained by cosynthesis of two new *Actinoplanes missouriensis* strains, CUC 014 and CSV 558. Cultures CUC 014 and CSV 558 are the subject of a copending application of Charles L. Hershberger entitled NOVEL BIOCONVERTING MICROORGANISMS, docket No. X-6068, Ser. No. 544,337, filed Oct. 21, 1983, now U.S. Pat. No. 4,587,218, issued May 6, 1986. *A. missouriensis* strains CUC 014 and CSV 558 have been deposited and made a part of the stock culture collection of the Northern Regional Research Center, Agricultural Research, North Central Region, 1815 North University Street, Peoria, Ill. 61604, from which they are available to the public under the accession numbers NRRL 15646 (CSV 558) and NRRL 15647 (CUC 014).

Following the discovery that antibiotic CUC/CSV was produced by cosynthesis of the two *A. missouriensis* strains CUC 014 and CSV 558, it was discovered that this antibiotic could also be prepared by bioconversion of actaplanin factor A using either culture CUC 014 or culture CSV 558. These methods are disclosed in the copending application of LaVerne Boeck, Gladys M. Clem, Marie T. Anderson and Karl H. Michel entitled GLYCOPEPTIDE BIOCONVERSION PRODUCTS, docket No. X-6411, Ser. No. 544,332, filed Oct. 21, 983, now abandoned.

It was also subsequently discovered that antibiotic CUC/CSV is a minor factor produced by the actaplanin-producing culture *A. missouriensis* ATCC 31683. Antibiotic CUC/CSV was then assigned the designation factor "J" of the A-4696 (actaplanin) complex.

This invention also relates to methods of treating certain infections with, methods of increasing feed-utilization efficiency with, and a method of improving milk production in lactating ruminants with, and pharmaceutical compositions comprising, antibiotic CUC/CSV or a pharmaceutically acceptable salt of CUC/CSV together with a suitable carrier.

New, improved antibiotics are continually in demand. In addition to antibiotics which are useful for treating human diseases, improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer body half life, and more advantageous rate or route of excretion and rate or pattern of metabolism) are some of the goals for improved antibiotics.

Antibiotic CUC/CSV forms salts, particularly acid addition salts. These acid addition salts are also useful as antibiotics and are a part of this invention. In another aspect, such salts are useful as intermediates, for example, for separating and purifying the derivatives.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicyclic, methanesulfonic, benzenesulfonic, sorbic, picric, benzoic, cinnamic, and like acids.

Pharmaceutically acceptable acid addition salts are an especially preferred group of salts of this invention.

In the process provided by this invention, antibiotic CUC/CSV is produced by cosynthesizing the *A. missouriensis* strains CSV 558 (NRRL 15646) and CUC 014 (NRRL 15647). Cosynthesis is achieved by fermenting the secretor culture CUC 014 and the converter culture CSV 558 together under submerged aerobic conditions in a suitable culture medium until substantial antibiotic activity is produced. When fermented separately, neither culture CUC 014 nor CSV 558 produces antibiotic activity.

As will be appreciated by those in the art, the culture media used to grow the cosynthesizing *A. missouriensis* strains can be any one of a number of media (see, for example, U.S. Pat. No. 4,322,406 for a description of the media variations useful for the parent *A. missouriensis* ATCC 31683 strain). When cosynthesizing antibiotic CUC/CSV, the fermentation can be carried out by inoculating a common medium with the two culture simultaneously. Alternatively, a growing culture of *A. missouriensis* CUC 014 can be established, and then combined with a growing culture of the CSV 558 strain.

Antibiotic production can be followed during the fermentation by testing samples of the broth against organisms known to be sensitive to this antibiotic. One useful assay organism is *Bacillus subtilis*. The bioassay is conveniently performed by paper-disc assay on agar plates. In addition, antibiotic production can be monitored by high performance liquid chromatography (HPLC) with UV detection.

Following its production under submerged aerobic fermentation conditions, antibiotic CUC/CSV can be recovered from the fermentation medium by methods recognized in the art, e.g. adsorptive and extractive procedures.

Alternatively, the culture solids, including medium constituents and mycelium, can be used without extraction or separation, but preferably after removal of water, as a source of antibiotic CUC/CSV. For example, after production of antibiotic CUC/CSV, the whole fermentation broth can be dried by lyophilization, by drum-drying, or by azeotropic distillation and drying. The dried whole broth can then be mixed directly into feed premix.

Antibiotic CUC/CSV can also be prepared by bioconversion of actaplanin factor A using either culture CUC 014 or culture CSV 558 (see the co-pending application of Gladys. M. Clem, LaVerne D. Boeck, Marie T. Anderson, and Karl H. Michel entitled GLYCOPEPTIDE BIOCONVERSION PRODUCTS, docket No. X-6411, Ser. No. 544,332, filed Oct. 21, 1983 now abandoned.

Antibiotic CUC/CSV inhibits the growth of pathogenic bacteria, especially gram-positive bacteria. Table I summarizes the minimal inhibitory concentrations (MIC's) at which CUC/CSV inhibits certain organisms, as determined by standard agar-dilution assays.

TABLE I

| In Vitro Activity of CUC/CSV | |
|---|---|
| Organism | MIC (mg/ml) |
| Staphylococcus aureus NRRL B313 | 8 |
| Staphylococcus aureus V41 | 8 |
| Staphylococcus aureus X400 | 16 |
| Staphylococcus aureus S13E | 8 |
| Staphylococcus epidermidis EPI1 | 16 |
| Staphylococcus epidermidis 222 | 8 |
| Streptococcus pneumoniae Park 1 | 0.5 |
| Streptococcus faecium ATCC 9790 | 4 |
| Streptococcus sp. group D 9960 | 4 |

Antibiotic CUC/CSV also inhibits the growth of anaerobic bacteria. Table II summarizes the susceptibility of various anaerobic isolates to CUC/CSV.

TABLE II

| Susceptibility of Anaerobic Bacterial Isolates to CUC/CSV | |
|---|---|
| Anaerobic Bacteria | MIC (μg/ml)[a] |
| Clostridium difficile 2994 | 1 |
| Clostridium perfringens 81 | 4 |
| Clostridium septicum 1128 | 4 |
| Eubacterium aerofaciens 1235 | 2 |
| Peptococcus asaccharolyticus 1302 | 4 |
| Peptococcus prevoti 1281 | 8 |
| Peptostreptococcus anaerobius 1428 | 2 |
| Peptostreptococcus intermedium 1264 | 4 |
| Propionibacterium acnes 79 | 1 |
| Bacteroides fragilis 111 | >128 |
| Bacteroides fragilis 1877 | >128 |
| Bacteroides fragilis 1936B | >128 |
| Bacteroides thetaiotaomicron 1438 | >128 |
| Bacteroides melaninogenicus 1856/28 | >128 |
| Bacteroides melaninogenicus 2736 | 16 |
| Bacteroides vulgatis 1211 | >128 |
| Bacteroides corrodens 1874 | >128 |
| Fusobacterium symbiosum 1470 | >128 |
| Fusobacterium necrophorum 6054A | 2 |

[a]MIC's were determined by the agar-dilution method; endpoints were read after 24-hours incubation.

CUC/CSV has also shown in vivo antimicrobial activity against experimentally-induced bacterial infections. When two doses of test compound were administered to experimentally infected mice, the activity observed was measured as an $ED_{50}$ value [effective dose in mg/kg to protect 50% of the test animals: see Warren Wick et al., *J. Bacteriol.* 81, 233–235 (1961)]. $ED_{50}$ values observed for CUC/CSV are given in Table III.

TABLE III

| $ED_{50}$ Values for CUC/CSV in Mice | |
|---|---|
| Infecting Organism | $ED_{50}$ (mg/kg/2)[a] |
| Staphylococcus aureus | 1.59 |
| Streptococcus pyogenes | 1.09 |
| Streptococcus pneumoniae | 0.84 |

[a]administered subcutaneously 1 and 4 hours post-infection

This invention also relates to a method of controlling bacterial infections. In carrying out the method of this invention, an effective amount of a CUC/CSV compound is administered parenterally or orally to an infected or susceptible warm-blooded animal. The compound can also be administered by insufflation, i.e. by blowing the compound, in the form of a medicated dust, into an enclosed space or room wherein the animals or poultry are held. The animals or poultry breathe the medicated dust present in the air; the medicated dust is also taken into the body through the eyes (a process called intraocular injection).

The dose which is effective to control the infection will vary with the severity of the infection and the age, weight, and condition of the animal. The total dose required for protection parenterally will generally, however, be in the range of from about 0.1 to about 100 mg/kg and preferably will be in the range of from about 0.5 to about 50 mg/kg. The dose required for oral administration will generally be in the range of from 1 to about 300 mg/kg and preferably will be in the range of from about 1 to about 100 mg/kg. Suitable dosage regimens can be constructed.

Often the most practical way to administer the compounds is by formulation into the feed supply or drinking water. A variety of feeds, including the common dry feeds, liquid feeds, and pelleted feeds, may be used.

In another aspect, this invention relates to compositions useful for the control of bacterial infections. These compositions comprise a CUC/CSV compound together with a suitable vehicle. Compositions may be formulated for parenteral or oral administration by methods recognized in the pharmaceutical art.

Effective injectable compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions require a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

In another embodiment, this invention relates to methods of increasing feed-utilization efficiency and promoting growth rates in poultry, swine, sheep and cattle and of enhancing milk production in lactating ruminants. For increasing feed utilization efficiency and promoting growth, a CUC/CSV compound is administered orally in a suitable feed in an amount of from about 2 to about 200 grams per ton of total feed. For enhancing milk production in lactating ruminants, oral administration of a daily amount of from about 0.01 to about 10 mg/kg of body weight (or about 100 to about 1600 mg/ruminant/day) is suggested.

The methods of formulating drugs into animal feeds are well-known. A preferred method is to make a concentrated-drug premix which in turn is used to prepare medicated feeds. Typical premixes may contain from about 1 to about 200 grams of drug per pound of premix. Premixes may be either liquid or solid preparations.

The final formulation of feeds for animals or poultry will depend upon the amount of drug to be administered. The common methods of formulating, mixing, and pelleting feeds may be used to prepare feeds containing a CUC/CSV compound.

The following examples illustrate this invention.

EXAMPLE 1

Production of Antibiotic CUC/CSV by Cofermentation of Cultures CUC 014 and CSV 558

A. Shake-Flask Fermentation of Cultures CUC 014 and CSV 558

A lyophilized pellet of *Actinoplanes missouriensis* strain CUC 014 (NRRL 15647) or strain CSV 558 (NRRL 15646) is dissolved in 1–2 ml of sterilized water. This suspension is used to inoculate an agar slant having the following composition:

| Ingredient | Amount (%) |
|---|---|
| Precooked Oatmeal | 6.0 |
| Yeast | 0.25 |
| $K_2HPO_4$ | 0.1 |
| Czapek Mineral Stock[a] | 0.5 |
| Agar[b] | 2.5 |
| Deionized $H_2O$ | q.s. to 100% |
| Unadjusted pH = 6.2; adjust to pH 7.3 with 5 N NaOH; after sterilization pH = 6.7. | |

[a]Czapek Mineral Stock:

| Ingredient | Amount % |
|---|---|
| KCl | 10.0 |
| $MgSO_4.7H_2O$ | 10.0 |
| $FeSO_4.7H_2O$ | 0.2 (dissolved in 2 ml of Conc. HCl) |
| Deionized water | q.s. to 100% |

[b]Difco Laboratories

The inoculated slant is incubated at 30° C. for about eight to ten days. The mature slant culture is scraped with the serrated edge of a sterile loop to macerate and loosen the mycelial mat. About one-fourth of the loosened mat is used to inoculate 50 ml of a vegetative medium having the following composition:

| Ingredient | Amount (%) |
|---|---|
| Glucose | 2.0 |
| Tryptone[a] | 0.5 |
| Yeast Extract | 0.5 |
| Tap $H_2O$ | q.s. to 100% |
| Before sterilization, pH = 6.5; adjust to pH 7.2 with 5 N NaOH; after sterilization, pH = 6.9; | |

[a]Bacto Tryptone, Difco

The inoculated vegetative medium is incubated in a 250-ml Erlenmeyer flask at 30° C. for about 72 hours on a rotary shaker with a two-inch throw at 250 RPM.

Vegetative cultures can be initiated with agar-slant cultures, with lyophilized pellets of the culture (one lyophile per 50 ml of media in a 250-ml flask) and with cultures preserved in liquid nitrogen (0.8% inoculum).

Incubated vegetative medium (5%, volume/volume) is used to inoculate 50 ml of a production medium having the following composition:

| Ingredient | Amount (%) |
|---|---|
| Glucose | 2.5 |
| Corn Starch | 3.5 |
| Blackstrap Molasses | 1.5 |
| Glycerol | 1.5 |
| Yeast | 2.0 |
| $K_2HPO_4$ | 0.05 |
| $(NH_4)_2SO_4$ | 0.025 |
| $CaCO_3$ | 0.2 |
| Tap $H_2O$ | q.s. to 100% |
| Before sterilization pH = 6.5; adjust to 6.8; after sterilization pH = 6.5. | |

The inoculated production medium is incubated in a 250-ml Erlenmeyer flask at 30° C. for 72 hours on a 2-inch rotary shaker at 250 RPM.

B. Cosynthesis of Antibiotic CUC/CSV

After cultures CUC 014 and CSV 558 have fermented for 72 hours separately, equal volumes of whole broth from each fermentation are combined aseptically in a sterile flask. The flasks are incubated at 30° C. on a rotary shaker for an additional 96 hours.

C. Assay for Antibiotic CUC/CSV

Whole broth (adjusted to pH 10.5) is centrifuged. The supernatant is readjusted to pH 7.0. Samples thus prepared are assayed by a *Bacillus subtilis* plate assay and by thin-layer chromatography using silica-gel plates (Merck, pre-coated plastic sheets; silica gel 60, without fluorescent indicator) and an acetone:water:ammonia (160:40:1) solvent system. Detection was by bioautography using *B. subtilis* in a minimal growth medium and incubating plates at 37° C. for about 18 hours.

EXAMPLE 2

Isolation of Antibiotic CUC/CSV

Three lots of whole fermentation broth, prepared using procedures like that of Example 1, were combined (total volume=45 L.). This broth was centrifuged using a Cepa centrifuge. The mycelia were extracted twice with water at pH 10.5 (adjusted with sodium hydroxide). The extracts were combined (24 L.), adjusted to pH 7.0 with hydrochloric acid and applied to a column containing 40 L. of Diaion HP-20 (Mitsubishi Chemical Industries, Limited, Tokyo, Japan) at a flow rate of 160 ml/minute. The column was washed successively with 8 L. of water and 12 L. of methanol:water (1:3) and then was eluted with 8 L. of methanol:water (1:1), 8 L. of methanol:water (3:1), and 20 L. of methanol, collecting 4-L fractions. Each fraction was analyzed for biological activity. The bioassay was performed by a paper-disc assay on agar plates seeded with *Bacillus subtilis*. Fractions containing the desired activity were combined, concentrated under reduced pressure and lyophilized to give 10.1 g of crude material.

A portion of this material (0.5 g) was dissolved in 15 ml of methanol:water (3:2) and filtered. The filtrate was applied to a 5.2-×41-cm Michel-Miller HPLPLC glass column packed with 590 ml of 25-40 micron Lichroprep RP-18 reversed-phase silica gel from MC/B Manufacturing Chemist, Inc., Cincinnati, OH. The column was eluted with (35:65) methanol:potassium dihydrogen phosphate buffer (0.05M adjusted to pH 3.5 with phosphoric acid) at a rate of 10 ml/minute, collecting 20-ml fractions. The eluate was monitored at 280 nm using an Isco Model UA-5 UV monitor with a Type 6 optical unit (Instrumentation Specialties Co., Lincoln, NE). All fractions were analyzed by padding paper disks on agar plates containing a minimal media seeded with *Bacillus subtilis*. Fractions having the desired activity were combined, adjusted to pH 7.0 with sodium hydroxide and concentrated under reduced pressure. The concentrated pool (100 ml) was applied to a column packed with 90 ml of Diaion HP-20. The column was washed with 400 ml of water and then eluted with acetonitrile:water (4:1). The first eluate (29 ml) was discarded, and the next eluate (15 ml) was collected, concentrated under reduced pressure and lyophilized to give 27 mg of pure antibiotic CUC/CSV. CUC/CSV has the following characteristics:

Elemental Analysis:

|  | Calc.[a] | Found |
| --- | --- | --- |
| C-90 | 49.46 | 49.28 |
| H-98 | 5.63 | 4.35 |
| N-7 | 4.49 | 4.55 |
| O-41 | 38.80 | 39.82 (by difference) |
| Cl-1 | 1.62 | 2.00 |

[a]for $C_{90}H_{98}N_7O_{41}Cl.12H_2O$

Ultraviolet Absorption (in methanol):
$\lambda_{max}$ 278 nm, acid ($\epsilon \sim 17,000$)
$\lambda_{max}$ 277 nm, 361 nm, neutral ($\epsilon \sim 18,500, 9,000$)
$\lambda_{max}$ 295 nm, 340 nm, base ($\epsilon \sim 21,000, 14,500$)
Calculated on a molecular weight of 1200. The compound shows end-absorption at 230 nm.

Solubility:
soluble in dimethyl sulfoxide, dimethylformamide, acetonitrile:water, and alcohol:water mixtures.

Mass Spectrometry (Fast Atom Bombardment):
FAB MS indicates a molecular weight of 1968.

EXAMPLE 3

Preparation of CUC/CSV by Bioconversion of Actaplanin Factor A with Culture CSV 558

A. The Bioconversion

Actaplanin factor A (100 mg) was dissolved in water, sterilized by filtration, and added (final conc. of 0.3 mg/ml) to a five-day-old, one-liter fermentation of the converter culture *A. missouriensis* CSV 558 (NRRL 15646). The fermentation was incubated an additional 48 hrs. The pH of the whole broth was adjusted to 10.5 with NaOH; the broth was centrifuged, and the centrate was neutralized with HCl.

B. Isolation of CUC/CSV

A bioconversion was carried out using the procedure of Sect. A. The broth was removed by filtration, and the mycelia were extracted with water at pH 10.5. This extract (550 ml) was purified over a column packed with 100 ml of HP-20 as described in Example 2 to give a lyophilized crude product (190 mg). A portion of this product (100 mg), dissolved in 5 ml of $CH_3CN$:pyrOAc (36:64) at pH 3.6, was applied to a 300-ml glass column packed with Lichroprep RP-8 resin (25–40 μm). The column was eluted with $CH_3CN$:0.05% pyrOAc (1:4) at pH 3.6 at a flow rate of 8 ml/min. Product was detected by UV absorbance at 280 nm, by *B. subtilis* bioassay and by analytical HPLC. Fractions containing the desired activity were combined, adjusted to pH 6.5 with N NaOH, then concentrated to remove $CH_3CN$. The resulting aqueous solution (50 ml) was applied to a 40-ml column filled with 12 ml of LP1-C18 resin (see U.S. Pat. No. 4,293,482, Example 7) in water. The column was washed with water (100 ml) to remove the salt, and the active material was eluted with $CH_3CH:H_2O$ (7:3). The eluate was concentrated and lyophilized to give 10 mg of purified antibiotic CUC/CSV.

EXAMPLE 4

Preparation of CUC/CSV by Bioconversion of Actaplanin Factor A with Culture CUC 014

Following the procedure of Example 3, but using culture CUC 014 (NRRL 15647) instead of culture CSV 558, actaplanin factor A is converted to antibiotic CUC/CSV.

EXAMPLE 5

Analytical HPLC System For Antibiotic CUC/CSV

Column: 4.6-×250-mm stainless steel
Packing: Shandon ODS Hypersil-5 micron
Solvent: $CH_3CN$:0.05M $KH_2PO_4$ adjusted to pH 3.2 with $H_3PO_4$ (21:79)
  Flow Rate: 1.0 ml/min.
  Detection: UV at 220 nm.
  Chart speed: 20 cm/hr.
  Retention time: 9.3 minutes.

We claim:

1. The method of preparing antibiotic CUC/CSV which comprises cofermenting *Actinoplanes missouriensis* strains NRRL 15646, or a mutant or variant thereof which retains its characteristic ability to cosynthesize antibiotic CUC/CSV, and NRRL 15647, or a mutant or variant thereof which retains characteristic ability to cosynthesize antibiotic CUC/CSV under submerged aerobic fermentation conditions in a culture medium containing assimilable sources of carbon, nitrogen and inorganic nutrients until a substantial amount of antibiotic CUC/CSV is produced.

2. The method of claim 1 wherein the cofermented strains are NRRL 15646 and NRRL 15647.

3. The method of claim 1 which includes the additional step of isolating antibiotic CUC/CSV from the culture medium.

* * * * *